United States Patent
Becker et al.

(10) Patent No.: US 9,346,965 B2
(45) Date of Patent: May 24, 2016

(54) HEPTYL ESTERS OF FURAN DICARBOXYLIC ACID AS SOFTENERS

(75) Inventors: Hinnerk Gordon Becker, Essen (DE); Michael Grass, Haltern am See (DE); Andre Huber, Marl (DE); Michael Woelk-Faehrmann, Marl (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/001,597

(22) PCT Filed: Jan. 27, 2012

(86) PCT No.: PCT/EP2012/051325
§ 371 (c)(1),
(2), (4) Date: Oct. 8, 2013

(87) PCT Pub. No.: WO2012/113609
PCT Pub. Date: Aug. 30, 2012

(65) Prior Publication Data
US 2014/0024754 A1    Jan. 23, 2014

(30) Foreign Application Priority Data
Feb. 24, 2011 (DE) .......... 10 2011 004 677

(51) Int. Cl.
*C07D 307/68* (2006.01)
*C09D 7/12* (2006.01)
*C08K 5/00* (2006.01)
*C08K 5/1535* (2006.01)

(52) U.S. Cl.
CPC ............ *C09D 7/1233* (2013.01); *C07D 307/68* (2013.01); *C08K 5/0016* (2013.01); *C08K 5/1535* (2013.01)

(58) Field of Classification Search
USPC .......................... 524/111; 549/485; 106/316
See application file for complete search history.

(56) References Cited

U.S. PATENT DOCUMENTS

| 8,022,244 | B2 | 9/2011 | Grass et al. |
| 8,258,325 | B2 | 9/2012 | Grass et al. |
| 2007/0060768 | A1 | 3/2007 | Grass et al. |
| 2012/0202725 | A1 | 8/2012 | Grass et al. |
| 2012/0220507 | A1 | 8/2012 | Grass et al. |

FOREIGN PATENT DOCUMENTS

| JP | 2000-319444 A | 11/2000 |
| JP | 2008-127282 | 6/2008 |
| WO | WO 2005/037764 A1 | 4/2005 |
| WO | WO 2008/095571 A1 | 8/2008 |
| WO | WO 2008/155159 A1 | 12/2008 |
| WO | WO 2011/023491 A1 | 3/2011 |
| WO | WO 2011/023590 A1 | 3/2011 |
| WO | WO 2012/113608 A1 | 8/2012 |
| WO | WO 2012/130545 A1 | 10/2012 |

OTHER PUBLICATIONS

U.S. Appl. No. 14/008,425, filed Sep. 27, 2013, Becker, et al.
U.S. Appl. No. 14/001,177, filed Aug. 23, 2013, Becker, et al.
U.S. Appl. No. 14/001,338, filed Sep. 5, 2013, Becker, et al.
International Search Report issued Mar. 2, 2012 in Application No. PCT/EP2012/051325.
"Sales Specification EXXAL™ 7 Isoheptyl Alcohol", URL: http://www.imperialoil.ca/Canada-English/Files/Products_Chemicals/exxa17.pdf , Feb. 1, 2006, XP55019574, 1 page.
R. D. Sanderson, et al., "Synthesis and Evaluation of Dialkyl Furan-2,5-Dicarboxylates as Plasticizers for PVC", Journal of Applied Polymer Science, vol. 53, No. 13, Sep. 26, 1994, pp. 1785-1793.
P. A. Yoder, et al., "Ueber Dehydroschleimsaure: eine neue Darstellungsmethode, sowie verschiedene Salze und Ester derselben", Berichte Der Deutschen Chemischen Gesellschaft Abteilung B, vol. 34, No. 3, Oct. 1, 1901, pp. 3446-3462.
Leonard G. Krauskopf, et al., "Plasticizer Factors Influencing Take-Up by PVC Resins" ANTEC '99 Conference Proceedings, 57th vol. 3, May 26, 1999, pp. 3526-3536 and Cover Pages.
Rubber, et al., "Handbook—Rubber and Plastic Compounding Chemicals, 2nd Revision" K.K. Rubber Digest Sha, 1993, pp. 157-203 and Cover Pages (with partial English language translation).
Taisei-Sha "Revised new version—Plastic additives—base and application", K.K. first edition issued on Nov. 30, 1996, pp. 6 to 32 and Cover Pages (with partial English language translation).
ExxonMobil "Alkyl Alcohols C6 to C13 Category Analysis Report" 201-16244A, ExxonMobil Biomedical Sciences, Inc., Apr. 18, 2006, pp. 1-57 and Cover Page.

*Primary Examiner* — James J Seidleck
*Assistant Examiner* — Deve E Valdez
(74) *Attorney, Agent, or Firm* — Oblon, McClelland, Maier & Neustadt, L.L.P.

(57) ABSTRACT

The invention relates to the use of heptyl esters of furan dicarboxylic acid as softeners.

17 Claims, No Drawings

HEPTYL ESTERS OF FURAN DICARBOXYLIC ACID AS SOFTENERS

CROSS-REFERENCE TO RELATED APPLICATIONS

This application is a National Stage of PCT/EP2012/051325 filed on Jan. 27, 2012. This application is based upon and claims the benefit of priority to German Application No. 10 2011 004 677.1 filed on Feb. 24, 2011.

The present invention relates to heptyl esters of furandicarboxylic acid.

The invention further provides for the use of the heptyl esters as or in plasticizers and in compositions, especially in those comprising polymers, especially PVC, and a preparation process for these heptyl esters. The invention further provides polymer compositions comprising these heptyl esters and mouldings or films produced from or using these polymer compositions.

Polyvinyl chloride (PVC) is one of the most economically important polymers and is used in various applications both in the form of rigid PVC and in the form of flexible PVC. Important areas of use are, for example, cable sheathing, floor coverings, wallpaper and frames for plastic windows. To increase the elasticity and for better processability, plasticizers are added to the PVC. These customary plasticizers include, for example, phthalic esters such as di-2-ethylhexyl phthalate (DEHP), diisononyl phthalate (DINP) and diisodecyl phthalate (DIDP). Due to their toxicological properties, there are efforts to replace phthalic esters with other plasticizers. Alternative plasticizers which have been described recently are therefore, for example, cyclohexanedicarboxylic esters such as diisononyl cyclohexanedicarboxylate (DINCH).

In addition, the prior art has also described esters of terephthalic acid as alternative plasticizers.

With regard to the raw material basis, the distinctive feature of the present invention lies in the optional use of renewable raw materials to produce the inventive furandicarboxylic esters. In the context of the present invention, renewable raw materials, in contrast to petrochemical raw materials based on fossil resources, for example mineral oil or hard coal, are understood to mean those raw materials which form or are produced on the basis of biomass. The terms "biomass", "biobased" or "based on and produced from renewable raw materials" encompass all materials of biological origin which originate from what is called the "short-term carbon cycle", and are thus not part of geological formations or fossil strata. Renewable raw materials are identified and quantified according to ASTM method D6866. One characteristic feature of renewable raw materials is the proportion of the carbon isotope $^{14}C$ therein as contrasted with petrochemical raw materials.

It is known that, with increasing alkyl chain length of the esters, there is a rise in the incompatibility thereof with polymers, especially with PVC. This can have the consequence, for example, that the PVC compositions which contain such molecules, for example as plasticizers, exhibit atypical and unforeseeable viscosity profiles which complicate processing of the PVC plastisols. In the production of films, it is often found that they have an increasingly nontransparent appearance and/or discoloration of the film occurs, which is reflected, for example, in an increased yellowness which is undesirable in most applications, A lower compatibility of plasticizers and PVC also reduces the permanence of the plasticizer, which means that these plasticizers escape relatively rapidly from the semifinished or finished PVC product, which leads to embrittlement of the product and hence to a significant reduction in the function and value of the corresponding product. The behaviour of the plasticizer is also referred to as "exudation" or "sweating".

Secondly, it is also known that esters with short alkyl chains generally firstly have relatively high volatility, but secondly also, especially where esters with high gelating capacity are concerned, lead when processed in PVC pastes to pastes with low storage stability, the shear viscosity of which frequently depends very greatly on the shear rate, which again leads to restricted processability.

In the production of PVC plastisols, particular care should be taken that a minimum viscosity is maintained in the course of processing in order to achieve homogeneous distribution of the plasticizer in the PVC. Furthermore, high storage stability of the PVC plastisol and low dependence of the shear viscosity of the paste on the shear rate are also desirable. Unfilled films produced from PVC plastisols should be transparent and have minimum yellowness. The plasticizer should additionally have high permanence.

In the prior art, various alternative plasticizers have become known for use in PVC. EP 1 808 457 A1 describes the use of dialkyl terephthalates, which are characterized in that the alkyl radicals have a longest carbon chain of at least 4 carbon atoms and have a total number of carbon atoms per alkyl radical of 5. It is also stated that terephthalic esters having 4 or 5 carbon atoms in the longest carbon chain of the alcohol have good suitability as fast-gelating plasticizers for PVC.

Similarly, WO 2009/095126 A1 describes mixtures of diisononyl esters of terephthalic acid and processes for preparation thereof. These plasticizers have an average degree of branching of the isononyl radicals which is in the range from 1.0 to 2.2 and are likewise used as plasticizers for PVC.

Terephthalic esters of alcohols having 7 carbon atoms and use thereof as plasticizers are described, for example in WO 2010/071717 A1.

Many esters of furandicarboxylic acid, for example di-n-butyl furan-2,5-dicarboxylate and di-n-hexyl furan-2,5-dicarboxylate, are room temperature crystalline solids which, being solids, can be used only with difficulty, it all, for the production of liquid compositions, especially of (polymer) plastisols. Thus, the production of polymer pases or plastisols on the industrial scale can be achieved only with liquid plasticizers. Solid plasticizers have to be dissolved beforehand in appropriate solvents, which makes the process inconvenient and costly.

The technical object of the invention was therefore to provide compounds which can be used as or in plasticizers and which can also be processed in plastisols, have good gelation properties, exhibit low dependence of the paste viscosity on the shear rate in plastisols, and have good yellowness and high transparency when processed to give films. It was an additional object to implement the solution to this technical objective in connection with a substance or compound which can be produced at least partly from renewable raw materials.

This technical object is achieved by heptyl esters of furandicarboxylic acid.

The heptyl esters are preferably diheptyl esters.

More particularly, the technical object is achieved by heptyl esters of furandicarboxylic acid which have at least one of the following properties:
1) density at 20° C. is not more than 1.1 g/cm$^3$;
2) intrinsic viscosity at 25° C. is not more than 120 mPa*s;
3) when analyzed with a differential calorimeter, there is no melting signal at temperatures >20° C.

In a further embodiment, the heptyl ester has at least two of the abovementioned properties.

It has been found that, surprisingly, such inventive heptyl esters, unlike the corresponding homologous butyl and hexyl esters, are not solids and have good processability as liquids at room temperature. The corresponding homologous di-n-butyl furandicarboxylates and di-n-hexyl furandicarboxylates are solid at room temperature and have melting points in the range of 30-40° C. They therefore cannot be used on the industrial scale for production of polymer pastes or plastisols.

Di-n-butyl furandicarboxylate and di-n-hexyl furandicarboxylate are known from the studies of Sanderson et al (R. D. Sanderson, D. F. Schneider, I. Schreuder; J. Appl. Polym. Sci.; 53 (1991); 1785-1793). These are crystalline solids with melting points of approx. 42° C. (di-n-butyl furandicarboxylate) and approx. 32° C. (di-n-hexyl furandicarboxylate), which cannot be used viably for numerous applications, for example the production of polymer pastes.

Diheptyl esters of furandicarboxylic acid have not been described to date; more particularly there are no suggestions to use diheptyl esters of furandicarboxylic acid in polymer compositions and/or as plasticizers.

It has now been found that, surprisingly, the inventive heptyl esters can be produced in liquid form without solidification, and can be used advantageously as a component in polymer formulations, for example as plasticizers in PVC formulations.

It has additionally been found that the inventive heptyl esters have excellent gelation properties when they are processed with PVC.

The PVC pastes based on the inventive heptyl esters have only a low dependence of the paste viscosity on the shear rate. They are thus processable within a wide shear rate range and with a wide variety of different processing methods.

Due to the favourable gelation characteristics, the corresponding PVC pastes can be processed more rapidly or at lower temperatures.

Blending with primary or secondary non-phthalate plasticizers, for example diisononyl cyclohexanecarboxylate (DINCH) which has a much poorer plasticizing action, also worsens the plasticizer efficiency of the inventive heptyl esters of furandicarboxylic acid (DIHFDC) only insignificantly.

It is also found that the test specimens which comprise an inventive heptyl ester have much lower losses of mass at elevated temperature than test specimens which comprise hexyl esters of furandicarboxylic acid as plasticizers. The test specimens containing the inventive heptyl esters thus have much better stability at elevated temperature.

A further advantage of the inventive plasticizer is that samples which comprise the inventive plasticizer have a much better thermal stability than samples comprising diisononyl cyclohexanecarboxylate (DINCH) as the sole plasticizer, di-n-hexyl furandicarboxylate (DNHFDC) as the sole plasticizer and di(2-ethylhexyl)furandicarboxylate (D2EHFDC) in a blend with DINCH.

Test specimens comprising the inventive heptyl esters additionally exhibit, in the region of >0° C., a much higher flexibility both in the form of test specimens comprising linear DNHFDC and in the form of test specimens comprising the singly branched D2EHFDC which is one carbon atom "longer". The inventive sample also has a much higher flexibility compared to the D2EHFDC sample at 0° C. and at −30° C. This is all the more astonishing in that the glass transition temperature of the inventive sample is higher compared to the two other samples, and the flexibility of flexible PVC test specimens generally rises with decreasing glass transition temperature.

It has additionally been found that transparent PVC films which comprise the inventive plasticizer also give products having a very high transparency, which is in some cases higher than that of films which have been produced with dibutyl terephthalate as a plasticizer.

A particular economic and simultaneously environmental advantage of the present invention lies in the simultaneous use of renewable and petrochemical raw materials for the production of the inventive furandicarboxylic esters, which firstly enables particularly inexpensive production and wide usability, but secondly also leads to particularly "sustainable" products.

In a preferred embodiment, the heptyl ester of furandicarboxylic acid is a diheptyl furan-2,5-dicarboxylate. This may also be present in the form of at least two isomeric diheptyl furan-2,5-dicarboxylates.

In a preferred embodiment, plasticizers composed of isomeric diheptyl furan-2,5-dicarboxylates are therefore also used, the latter comprising isomeric heptyl groups selected in particular from n-heptyl, 2-methylhexyl, 3-methylhexyl, 4-methylhexyl, 5-methylhexyl, 2,2-dimethylpentyl, 2,3-dimethylpentyl, 3,3-dimethylpentyl, 2,4-dimethylpentyl, 3-ethylpentyl, 2,2,3-trimethylbutyl or 2-ethyl-3-methylbutyl groups.

In a particular embodiment, at least 70 mol % of all alkyl ester chains (irrespective of their conformation) consist of 7 carbon atoms, preferably at least 80 mol %, more preferably at least 90 mol % and especially preferably at least 92 mol %. The alkyl chains having fewer or more than 7 carbon atoms are more preferably those having 6 or 8 carbon atoms. They are especially preferably 2,3-dimethylbutyl, 2-ethylbutyl, 4-methylpentyl or 3-methylpentyl groups.

In a preferred embodiment, none of the isomeric diheptyl furan-2,5-dicarboyxlates has a proportion of more than 90% by weight in the isomeric ester mixture.

The percentage distribution of the C7-alkyl radicals can be determined in a simple manner by hydrolyzing the esters, removing the alcohol obtained and analyzing the alcohol by gas chromatography (GC). For example, the gas chromatography separation can be performed on a polydimethylsiloxane column (e.g. DB 5) as the stationary phase with a length of 60 m, an internal diameter of 0.25 mm and a film thickness of 0.25 µm.

Further additional plasticizers excluding heptyl esters of furandicarboxylic acid may preferably be present.

Such additional plasticizers are, for example, selected from the following list:

dialkyl phthalates, preferably having 4 to 13 carbon atoms in the alkyl chain; trialkyl trimellitates, preferably having 4 to 9 carbon atoms in the side chain; dialkyl adipates, preferably having 4 to 9 carbon atoms in the side chain; dialkyl terephthalates, preferably each having 4 to 13 carbon atoms, especially 4 to 9 carbon atoms, in the side chain; alkyl 1,2-cyclohexanedicarboxylates, alkyl 1,3-cyclohexanedicarboxylates and alkyl 1,4-cyclohexanedicarboxylates, preference being given here to alkyl 1,2-cyclohexanedicarboxylates, preferably in each case with 4 to 10 carbon atoms in the side chain; dibenzoic esters of glycols; alkylsulphonic esters of phenol with preferably one alkyl radical containing 8 to 22 carbon atoms; glyceryl esters; isosorbide esters, especially isosorbide dialkanoates; epoxidized vegetable oils, especially epoxidized soybean oil; saturated or unsaturated fatty acid esters which (in the unsaturated case) may be fully or partially epoxidized; citric triesters with a free or carboxylated OH group and, for example, alkyl radicals of 4 to 8 carbon atoms, alkylpyrrolidone derivatives with alkyl radicals of 4 to 18 carbon atoms and alkyl benzoates, preferably with 7 to 13 carbon atoms in the alkyl chain. In all cases, the alkyl radicals may be linear or branched and identical or different.

More preferably, in the inventive mixtures, no ortho-phthalate is used as additional plasticizer.

In a particular embodiment, at least one of the additional plasticizers used in the inventive composition is a trialkyl trimellitate. This trialkyl trimellitate preferably has ester side chains having 4 to 9 carbon atoms, where the ester groups may have either the same or a different number of carbon atoms. More preferably, at least one of the ester groups present is a group having not more than 8 carbon atoms per ester group, especially preferably a group having not more than 7 carbon atoms and most preferably a group having not more than 6 carbon atoms. The combination of the inventive diheptyl furandicarboxylates with trialkyl trimellitates, when used in PVC plastisols, leads especially to products which have a low proportion of volatile constituents and good thermal stability.

In a further particular embodiment, at least one of the additional plasticizers used in the inventive composition is a dialkyl adipate. This dialkyl adipate preferably has ester side chains having 4 to 9 carbon atoms, where the ester groups here too may have either the same or a different number of carbon atoms. More preferably, at least one of the ester groups present is a group having not more than 8 carbon atoms per ester group, especially preferably a group having not more than 7 carbon atoms and most preferably a group having not more than 6 carbon atoms. More particularly, at least one of the dialkyl adipates used is dioctyl adipate. The combination of the inventive diheptyl furandicarboxylates with dialkyl adipates, when used in PVC plastisols, leads especially to products which have a low plastisol viscosity and, in the processed state, good low-temperature properties (for example a very low glass transition temperature).

In a further particular embodiment, at least one of the additional plasticizers used in the inventive composition is a dialkyl terephthalate. This dialkyl terephthalate preferably has ester side chains having 4 to 13 carbon atoms, where the ester groups may again have either the same or a different number of carbon atoms. More preferably, at least one of the ester groups present is a group having not more than 10 carbon atoms per ester group, especially preferably a group having not more than 9 carbon atoms and most preferably a group having not more than 8 carbon atoms. More particularly, at least one of the dialkyl terephthalates used is di(isononyl)terephthalate, di(2-ethylhexyl)terephthalate, di-n-heptyl terephthalate, diisoheptyl terephthalate, di-n-butyl terephthalate, di(3-methylbutyl)terephthalate or di-n-pentyl terephthalate. The combination of the inventive diheptyl furandicarboxylates with dialkyl terephthalates, when used in PVC plastisols, leads especially to products which (according to the ester chain length of the dialkyl terephthalates used) have a very good thermal stability and good low-temperature properties with a simultaneously low level of volatile constituents.

In a further particular embodiment, at least one of the additional plasticizers used in the inventive composition is a dialkyl ester of cyclohexanedicarboxylic acid, more preferably a dialkyl ester of 1,2-cyclohexanedicarboxylic acid. Preferably, this dialkyl cyclohexanedicarboxylate has ester side chains having 4 to 10 carbon atoms, where the ester groups may again either have the same or a different number of carbon atoms. More preferably, at least one of the ester groups present is a group having not more than 9 carbon atoms per ester group, especially preferably a group having not more than 8 carbon atoms and most preferably a group having not more than 7 carbon atoms. More particularly, at least one of the dialkyl cyclohexanedicarboxylates used is di-iso-nonyl 1,2-cyclohexanedicarboxylate, di-2-ethylhexyl 1,2-cyclohexanedicarboxylate, di-n-pentyl 1,2-cyclohexanedicarboxylate, di-n-heptyl 1,2-cyclohexanedicarboxylate, di-iso-heptyl 1,2-cyclohexanedicarboxylate, di-n-butyl 1,2-cyclohexanedicarboxylate, di-n-butyl 1,4-cyclohexanedicarboxylate, di-n-butyl 1,3-cyclohexanedicarboxylate or di(3-methylbutyl) 1,2-cyclohexanedicarboxylate. The combination of the inventive diheptyl furandicarboxylates with dialkyl esters of cyclohexanedicarboxylic acid, when used in PVC plastisols, leads especially to products which have the particular features of very low plastisol viscosity with simultaneously good gelation properties.

In a further particular embodiment, at least one of the additional plasticizers used in the inventive composition is a glyceryl ester, more preferably a glyceryl triester. The ester groups may either be of aliphatic or aromatic structure. This glyceryl ester preferably has ester side chains having 1 to 24 carbon atoms, where the ester groups may again have either the same or a different number of carbon atoms. More preferably, one of the ester groups is hydroxystearic acid, where the hydroxyl function is preferably likewise esterified, more preferably by an acetyl group. Additionally more preferably, at least one of the ester groups present is a group having not more than 9 carbon atoms per ester group, especially preferably a group having not more than 8 carbon atoms and most preferably a group having not more than 7 carbon atoms. More particularly, at least one of the glyceryl esters used is a glyceryl triacetate. The combination of the inventive diheptyl furandicarboxylates with glyceryl esters leads especially to particularly sustainable products which can be produced to a large degree on the basis of renewable raw materials.

In a further particular embodiment, at least one of the additional plasticizers used in the inventive composition is a citric triester with a free or carboxylated OH group. The ester groups here too may be either of aliphatic or aromatic structure. The citric triester is especially preferably a trialkyl citrate with a carboxylated OH group. This trialkyl citrate preferably has ester side chains having 1 to 9 carbon atoms, where the ester groups may again have either the same or a different number of carbon atoms. More preferably, at least one of the ester groups present is a group having not more than 9 carbon atoms per ester group, especially preferably a group having not more than 8 carbon atoms and most preferably a group having not more than 7 carbon atoms. More particularly, at least one of the citric esters used is acetyl tributyl citrate, acetyl tri-n-butyl citrate, acetyl tri-n-pentyl citrate or acetyl tri-iso-heptyl citrate. The combination of the inventive diheptyl furandicarboxylates with citric triesters with a free or carboxylated OH group leads especially to plastisols which have particularly good gelating capacity, especially at low temperatures, and like the combination with citric esters can be classified as particularly sustainable with respect to the renewable raw materials used for production.

In a preferred embodiment, the mass ratio of additional plasticizers used to inventive heptyl esters is between 1:20 and 20:1, preferably between 1:15 and 15:1, more preferably between 1:10 and 15:1 and especially preferably between 1:10 and 10:1.

The inventive heptyl esters or the plasticizers produced therefrom may be present in all possible presentation forms, for example as a liquid, especially as a pumpable liquid (pumpable at room temperature), as a paste, protective composition, plastisol, powder or solid. Especially preferably, they are present in liquid form and especially preferably in the form of a pumpable liquid (pumpable at room temperature).

In addition to the heptyl ester itself, a process for preparation thereof is also claimed.

Process for preparing an above-described heptyl ester, comprising the process steps of:
a) contacting furandicarboxylic acid and/or at least one furandicarboxylic acid derivative, especially dimethyl furandicarboxylate or furandicarbonyl chloride, with one or more aliphatic alcohols having 7 carbon atoms, or an alcohol mixture of aliphatic alcohols of which >80 mol % have 7 carbon atoms, and optionally one or more esterification catalysts and/or further substances,
b) heating the reaction mixture described to a temperature of >50° C. and esterifying or transesterifying while removing at least one low molecular weight substance from the reaction mixture, the removal in process step b) preferably being effected thermally.

In an alternative process for preparing an above-described heptyl ester, this process comprises the process steps of:
a) contacting 5-hydroxymethylfurfural and/or at least one furan derivative with one or more aliphatic alcohols having 7 carbon atoms and at least one catalyst and at least one oxygen-containing component,
b) adjusting the reaction mixture described to a temperature of >0° C. and conducting an oxidative esterification, the term "oxidative esterification" being understood to mean (any) combination of oxidation and esterification in preferably one process step, especially preferably in one reaction space.

The latter process is preferred here.

The heptyl esters can be prepared by "direct" esterification of the furandicarboxylic acid or by transesterification, for example from the methyl esters of the furandicarboxylic acid.

To prepare the inventive heptyl esters by means of esterification, either furandicarboxylic acid or a reactive derivative, for example the corresponding dichloride, is reacted with one or more aliphatic alcohols having 7 carbon atoms. The esterification preferably proceeds from furandicarboxylic acid and one or more aliphatic alcohols having 7 carbon atoms with the aid of a catalyst.

The esterification of the furandicarboxylic acid with one or more aliphatic alcohols having 7 carbon atoms to give the corresponding esters can be performed autocatalytically or catalytically, for example with Brønsted or Lewis acids. No matter what kind of catalysis is selected, the result is always a temperature-dependent equilibrium between the acid and alcohol feedstocks and the ester and water products. In order to shift the equilibrium in favour of the ester, it is possible to use an entraining agent, with the aid of which the water of reaction is removed from the mixture. Since the alcohols used for the esterification have a lower boiling point than the furandicarboxylic acid, the reactive derivatives thereof and esters thereof, they are frequently used as an entraining agent which, after removal of water, can be recycled back into the process.

The alcohol used to form the ester or the isomeric heptanol mixture which serves simultaneously as an entraining agent is used in an excess of preferably 5 to 50% by mass, especially 10 to 30% by mass, of the amount needed to form the ester.

The esterification catalysts used may be acids, e.g. Brønsted acids, for example sulphuric acid, methanesulphonic acid or p-toluenesulphonic acid, or metals or compounds thereof (generally Lewis acids). Suitable examples are tin, titanium, zirconium, which are used in the form of finely divided metals or appropriately in the form of salts thereof (e.g. halides), oxides or soluble or insoluble organic compounds. In contrast to protic acids, the metal catalysts are high-temperature catalysts which often attain their full activity only at temperatures above 180° C. However, it should be noted in this context that the furandicarboxylic acid tends to eliminate $CO_2$ (decarboxylation) at temperatures above 190° C. to form the monocarboxylic acid, which can no longer be converted to the target product.

However, the metal catalysts are used with preference because, compared to protic catalysis, they form a lower level of by-products, for example olefins from the alcohol used. Illustrative representatives of metal catalysts are tin powder, tin(II) oxide, tin(II) oxalate, titanic esters such as tetraheptyl orthotitanate, tetraisopropyl orthotitanate or tetrabutyl orthotitanate, and zirconium esters such as tetraheptyl zirconate or tetrabutyl zirconate.

The catalyst concentration depends on the type of catalyst. In the case of the titanium compounds used with preference, the concentration is 0.005 to 2.0% by mass based on the reaction mixture, especially 0.01 to 0.5% by mass, very preferably 0.01 to 0.1% by mass.

The reaction temperatures in the case of use of titanium catalysts are especially between 160° C. and 270° C., preferably 160° C. to 200° C. The optimal temperatures depend on the feedstocks, reaction progress and catalyst concentration. They can be determined easily by tests for each individual case. Higher temperatures increase the reaction rates and promote side reactions, for example elimination of water from alcohols or formation of coloured by-products. It is favourable for removal of the water of reaction that the alcohol can be distilled out of the reaction mixture. The desired temperature or the desired temperature range can be established by the pressure in the reaction vessel. In the case of low-boiling alcohols the reaction is therefore performed at elevated pressure, and in the case of higher-boiling alcohols under reduced pressure. For example, the reaction of furandicarboxylic acid with a mixture of isomeric heptanols is conducted within a temperature range of 160° C. to 190° C. within the pressure range from 0.1 MPa to 0.001 MPa.

The amount of liquid to be recycled into the reaction may consist partly or entirely of alcohol which is obtained by workup of the distillate. It is also possible to conduct the workup at a later time and to replace the amount of liquid removed completely or partially with fresh alcohol, i.e. alcohol available in a reservoir vessel.

The crude ester mixtures which comprise, in addition to the ester(s), alcohol, catalyst or conversion products thereof and possibly by-products are worked up by processes known per se. The workup comprises the following steps: removal of the excess alcohol and any low boilers, neutralization of the acids present, optionally a steam distillation, conversion of the catalyst to a readily filterable residue, removal of the solids and optionally drying. According to the workup process employed, the sequence of these steps may be different.

Optionally, the reaction product can be removed by distillation from the reaction mixture, optionally after neutralization of the mixture.

Alternatively, the inventive heptyl esters can be obtained by transesterifying a furan-2,5-dicarboxylic diester with one or more aliphatic alcohols having 7 carbon atoms. The reactants used are preferably furan-2,5-dicarboxylic diesters whose alkyl radicals bonded to the oxygen atom of the ester group have 1-4 carbon atoms. These radicals may be aliphatic, straight-chain or branched, and alicyclic or aromatic. One or more methylene groups of these alkyl radicals may be substituted by oxygen. It is appropriate that the parent alcohols of the reactant ester have a lower boiling point than the heptanol(s) used. A preferred feedstock is dimethyl furan-2,5-dicarboxylate.

The use of a furan-2,5-dicarboxylic diester for preparation of the inventive diheptyl furandicarboxylate is particularly advantageous because the furan-2,5-dicarboxylic diesters generally have a higher thermal stability than furan-2,5-dicarboxylic acid itself, and more particularly can also be purified without decomposition by thermal separating processes (for example distillation).

The transesterification can be performed catalytically, for example with Brønsted or Lewis acids or bases. No matter which catalyst is used, the result is always a temperature-dependent equilibrium between the feedstocks (dialkyl ester and heptanol or heptanol mixture) and the products (diheptyl ester or diheptyl ester mixture and alcohol released). In order to shift the equilibrium in favour of the diheptyl ester or of the diheptyl ester mixture, the alcohol formed from the reactant ester is distilled out of the reaction mixture.

It is also appropriate here to use the heptanol or the heptanol mixture in excess.

The transesterification catalysts used may be acids, for example sulphuric acid, methanesulphonic acid or p-toluenesulphonic acid, or metals or compounds thereof. Suitable examples are tin, titanium, zirconium, which are used in the form of finely divided metals or appropriately in the form of salts thereof (e.g. halides), oxides or soluble or insoluble organic compounds. Unlike protic acids, the metal catalysts are high-temperature catalysts which attain their full activity only at temperatures above 180° C. However, they are used with preference because they form a lower level of by-products compared to protic catalysis, for example olefins from the alcohol used. Illustrative representatives of metal catalysts are tin powder, tin(II) oxide, tin(II) oxalate, titanic esters such as tetraheptyl orthotitanate, tetraisopropyl orthotitanate or tetrabutyl orthotitanate, and zirconium esters such as tetraheptyl zirconate or tetrabutyl zirconate.

In addition, it is possible to use basic catalysts, for example oxides, hydroxides, hydrogencarbonates, carbonates or alkoxides of alkali metals or alkaline earth metals. From this group, preference is given to using alkoxides, for example sodium methoxide. Alkoxides can also be prepared in situ from an alkali metal and a heptanol or an isomeric heptanol mixture.

The catalyst concentration depends on the type of catalyst. It is typically between 0.005 to 2.0% by mass based on the reaction mixture.

The reaction temperatures for the transesterification are typically between 50° C. and 220° C. They must be at least sufficiently high that the alcohol formed from the reactant ester can be distilled out of the reaction mixture at the given pressure, usually standard pressure.

The transesterification mixtures can be worked up in the same way as described for the esterification mixtures.

In addition to direct esterification and transesterification, the inventive diheptyl furandicarboxylates can also be prepared by means of what is called oxidative esterification. This has the particular advantage that the intermediate of the furandicarboxylic acid or furandicarboxylic ester need not be separated, but rather can be worked up directly with the (semistable) intermediate, for example 5-hydroxymethylfurfural or another furan derivative. An additional factor is that generally low temperatures (i.e. lower tendency to form by-products) and relatively short reaction times are possible.

In order to enable the oxidation reaction, an oxygen-containing component must be present in the reaction mixture. Particularly advantageously suitable for this purpose are oxygen, air and/or peroxides, especially hydrogen peroxide.

The oxidative esterification is more preferably performed in the presence of a catalyst which significantly lowers the reaction time. The catalyst may either be a homogeneous or heterogeneous catalyst. The catalyst—the active catalyst surface in the case of hetereogeneous catalysts—more preferably has Lewis acidity. The catalyst is preferably a noble metal catalyst, in the case of a heterogeneous catalyst a noble metal catalyst with nanoscale surface especially a gold catalyst with nanoscale surface. In the case of heterogeneous catalysts, the use of an inorganic catalyst support is particularly advantageous, particular preference being given to macroporous or microporous supports, especially those which have pore surfaces with nanoscale structure.

In addition to the heptyl esters, the use thereof as or in plasticizer(s) for polymers is also claimed. The polymer is preferably a PVC.

In addition, the use of the inventive heptyl esters in adhesives, sealing compounds, coating compositions, lacquers, paints, plastisols, pastes, synthetic leather, floor coverings, underbody protection, fabric coatings, wallpaper or inks.

In addition, polymers or polymer compositions comprising at least one of the above-described heptyl esters or plasticizers are claimed.

The inventive plasticizers can be used in polymer compositions comprising at least one polymer. These polymers are preferably selected from the group consisting of: polyvinyl chloride (PVC), polyvinylidene chloride (PVDC), polyacrylates, especially polymethyl methacrylate (PMMA), polyalkyl methacrylate (PAMA), fluoropolymers, especially polyvinylidene fluoride (PVDF), polytetrafluoroethylene (PTFE), polyvinyl acetate (PVAc), polyvinyl alcohol (PVA), polyvinyl acetals, especially polyvinyl butyral (PVB), polystyrene polymers, especially polystyrene (PS), expandable polystyrene (EPS), acrylonitrile-styrene-acrylate copolymers (ASA), styrene acrylonitrile copolymers (SAN), acrylonitrile-butadiene-styrene copolymers (ABS), styrene-maleic anhydride copolymers (SMA), styrene-methacrylic acid copolymers, polyolefins and polyolefin copolymers, especially polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulphides (PSu), biopolymers, especially polylactic acid (PLA), polyhydroxybutyral (PHB), polyhydroxyvaleric acid (PHV), polyesters, starch, cellulose and cellulose derivatives, especially nitrocellulose (NC), ethylcellulose (EC), cellulose acetate (CA), cellulose acetate/butyrate (CAB), rubber or silicones, and mixtures or copolymers of the polymers mentioned or monomeric units thereof. The inventive polymer compositions preferably comprise PVC or homo- or copolymers based on ethylene, propylene, butadiene, vinyl acetate, glycidyl acrylate, glycidyl methacrylate, methyl acrylates, ethyl acrylates, butyl acrylates or methacrylates with alkyl radicals, bonded to the oxygen atom of the ester group, of branched or unbranched alcohols having one to ten carbon atom(s), styrene, acrylonitrile or cyclic olefins.

More preferably, the inventive polymer composition comprises, as the PVC type, suspension, bulk, microsuspension or emulsion PVC.

Based on 100 parts by mass of polymer, the inventive polymer compositions comprise preferably from 5 to 200, more preferably from 10 to 150, parts by mass of plasticizer. The mass ratio of plasticizer to polymer is 1:15 to 15:1, preferably 1:5 to 5:1.

The inventive polymer compositions may comprise, in addition to the constituents mentioned, further constituents which are especially selected from the group consisting of fillers, pigments, thermal stabilizers, costabilizers, antioxidants, viscosity regulators and lubricants.

The thermal stabilizers neutralize, for example, hydrochloric acid eliminated during and/or after the processing of PVC and prevent thermal degradation of the polymer. Useful thermal stabilizers include all customary stabilizers in solid and liquid form, for example based on Ca/Zn, Ba/Zn, Pb, Sn or organic compounds (OBS), and also acid-binding sheet silicates such as hydrotalcite. The inventive mixtures may have a content of 0.5 to 10, preferably 1 to 5 and more preferably 1.5 to 4 parts by mass of thermal stabilizer per 100 parts by mass of polymer.

The so-called costabilizers (i.e. substances which prolong, improve and/or supplement the effect of the thermal stabilizers) used may, for example, be vegetable oil derivatives, for example epoxidized soybean oil or epoxidized linseed oil.

The pigments used in the context of the present invention may be either inorganic or organic pigments. The content of pigments is between 0.01 to 10% by mass, preferably 0.05 to 5% by mass and more preferably 0.1 to 3% by mass per 100 parts by mass of polymer. Examples of inorganic pigments are $TiO_2$, CdS, $CoO/Al_2O_3$, $Cr_2O_3$. Known organic pigments are, for example, azo dyes, phthalocyanine pigments, dioxazine pigments and aniline pigments.

The inventive polymer compositions may comprise all fillers corresponding to the prior art. Examples of such fillers are mineral and/or synthetic and/or natural, organic and/or inorganic materials, for example calcium oxide, magnesium oxide, calcium carbonate, barium sulphate, silicon dioxide, sheet silicate, industrial carbon black, bitumen, wood (e.g. pulverized, as pellets, micropellets, fibres, etc.), paper, natural and/or synthetic fibres. More preferably, at least one of the fillers used is a calcium carbonate or a calcium magnesium carbonate.

The viscosity-lowering reagents used may be aliphatic or aromatic hydrocarbons, but also alcohols and/or carboxylic acid derivatives, for example 2,2,4-trimethyl-1,3-pentanediol diisobutyrate, or esters, e.g. long-chain alkyl benzoates. Viscosity-lowering reagents are added to the inventive compositions especially in proportions of 0.5 to 50, preferably 1 to 30 and more preferably 2 to 10 parts by mass per 100 parts by mass of polymer.

The invention further provides mouldings or films produced from or comprising the inventive polymer compositions. These mouldings or films are preferably a floor covering, a wall covering, a hose, a profile, a roofing sheet, a sealing sheet, a cable or wire sheath, a tarpaulin, an advertising banner, synthetic leather, packaging film, a medical article, a toy, a seal or a furnishing article.

The inventive diheptyl esters of furandicarboxylic acid, when used as plasticizers, have numerous advantages over known prior art plasticizers. For instance, these compounds are surprisingly, in contrast to the homologous di-n-butyl furandicarboxylates and di-n-hexyl furandicarboxylates, both of which are in the form of crystalline solids with melting points well above room temperature, liquids with good processability (including good meterability). The production of liquid compositions, especially polymer compositions such as polymer pastes and plastisols, on the industrial scale can best be implemented with liquid plasticizers since the use of solvents here is unnecessary. Solvents generally also lead to "dilution" of the plasticizing effect and therefore have to be removed again during the production. Since this can be accomplished quantitatively in the rarest cases, volatile (organic) components called "VOCs" are present in the semifinished or finished products, and are again prohibitive for the use of such products especially in the interior sector and in motor vehicles. An additional factor is the risk of crystallization of solid plasticizers in the semifinished or finished product, which leads to a severe deterioration in the material properties extending as far as material failure. The existing alternative solution to the use of solvents, that of using solid plasticizers in the molten state (i.e. at elevated temperature), cannot be implemented industrially in many cases. There is also the risk of thermal damage to other formulation constituents.

The thermal characteristics (especially the melting temperature and the occurrence of any glass transition point) of the inventive diheptyl furandicarboxylates depend on the degree of branching of the ester chains and the composition of the esters, and can be controlled via the composition of the alcohol mixture used to prepare the esters. In the analysis of the inventive diheptyl furandicarboxylates (purity by GC analysis at least 99 area %) in a differential calorimeter (DSC) after cooling to −150° C., no melting point occurs at temperatures above 20° C. in the first heating, preferably no melting point at temperatures above 10° C., more preferably no melting point at temperatures above 5° C. and especially preferably no melting point at temperatures above 0° C.

In a particular embodiment, especially when good low-temperature properties of the plasticizers or of the polymer compositions and mouldings are desired, at least 3 different isomers must be present in the alcohol mixture used to prepare the esters, preferably at least 4, more preferably at least 5 and especially preferably at least 6 isomers. In this case, in the analysis by means of DSC described, a glass transition temperature at <0° C. is detected, preferably at <−10° C., more preferably at <−20° C. and especially preferably at <−30° C.

The rheological characteristics, especially the shear viscosity of the inventive diheptyl furandicarboxylates depends on the degree of branching of the ester chains and the composition of the esters, and can likewise be controlled via the composition of the alcohol mixture used to prepare the esters. The shear viscosity, determined at 20° C., of the liquid inventive diheptyl furandicarboxylates (purity according to GC analysis at least 98 area %) depends on the degree of branching of the ester chains and the composition of the esters. It is especially not more than 120 mPa*s, preferably not more than 110 mPa*s, more preferably not more than 100 mPa*s and especially preferably below 95 mPa*s.

The density of the inventive esters likewise depends on the degree of branching of the ester chains and the composition of the esters, and is adjustable via the alcohols used to prepare the esters. The density, determined at 20° C., of the inventive esters (purity by GC analysis min 99 area %) is especially not more than 1.1 g/cm$^3$, preferably not more than 1.08 g/cm$^3$, more preferably not more than 1.06 g/cm$^3$ and especially preferably not more than 1.05 g/cm$^3$.

A further advantage is that these inventive heptyl esters have an outstanding gelation capacity for polymers, especially for PVC, and surprisingly also have a much lower dissolution temperature for PVC than, for example, di-n-butyl furandicarboxylate, even though they have a much longer ester chain. They can thus be processed rapidly and at low temperatures.

PVC plastisols/PVC pastes which comprise the inventive heptyl esters in a proportion of at least 10 ma % based on the plasticizers used overall attain, in the gelation test conducted by means of oscillating rheometry with dynamic temperature control (constant heating rate), especially a paste viscosity of >1000 Pa*s at temperatures of not more than 100° C., preferably of not more than 95° C., more preferably of not more than 90° C., especially preferably of not more than 85° C. and very especially preferably of not more than 80° C.

The temperature at which the maximum viscosity is attained in the above-described gelation test is especially not more than 120° C., preferably not more than 115° C., more preferably not more than 110° C., especially preferably not more than 105° C. and very especially preferably not more than 100° C.

It should also be emphasized that PVC pastes based on an inventive diheptyl ester of furandicarboxylic acid have only a low dependency of the paste viscosity on the shear rate. Thus, these plasticizers are usable within a wide shear rate range and with a wide variety of different processing methods.

PVC pastes based on the inventive heptyl esters additionally also have a much lower gelation temperature than, for example, diisononyl phthalate pastes. These can thus be processed more rapidly and at lower temperatures, and so higher-value products are the result.

The inventive plasticizers have further advantages over the plasticizers comprising hexyl esters or butyl esters of furan dicarboxylic acid. It has thus been found that test specimens comprising the inventive plasticizer have much better stability at elevated temperature because they have lower losses of mass. It has also been found that samples comprising the inventive plasticizer have a much better thermal stability than the comparative examples comprising the prior art plasticizers.

It has additionally also been found that, surprisingly, PVC films comprising the inventive heptyl esters as a plasticizer have very low opacity and hence high transparency. In some cases, this is much lower than in films which are produced on the basis of standard plasticizers.

More particularly, in the case of production of transparent films (film thickness 0.9-1.1 mm) from PVC plastisols/PVC pastes comprising the inventive heptyl esters in a proportion of at least 10 ma % based on the plasticizers used overall, opacity values of not more than 15 are achieved, preferably not more than 14, more preferably not more than 13, especially preferably not more than 12 and very especially preferably not more than 11. The yellowness index (index YD 1925) of the above-described transparent films is especially not more than 15, preferably not more than 14, more preferably not more than 13, especially not more than 12 and very especially preferably not more than 11.

By blending with diisononyl cyclohexanecarboxylate (DINCH) which has a much poorer plasticizing action, the plasticizer efficiency of the inventive heptyl esters of furandicarboxylic acid (DIHFDC) is worsened only insignificantly.

Test specimens comprising the inventive DIHFDC exhibit, at temperatures of >0° C., much higher flexibility (i.e. a lower storage modulus) both in the form of test specimens comprising linear DNHFDC and in the form of test specimens comprising the single branched D2EHFDC which is one carbon atom "longer". The inventive sample also has a likewise much higher flexibility compared to the D2EHFDC sample at 0° C. and at −30° C. This is all the more astonishing in that the glass transition temperature of the inventive sample is higher compared to the two other samples, and the flexibility of flexible PVC test specimens generally rises with decreasing glass transition temperature.

The examples which follow are intended to illustrate the invention, without restricting the range of application thereof, which is evident from the description and the claims.

EXAMPLES

Example 1

Preparation of furan-2,5-dicarbonyl dichloride (II)

The inventive esters were prepared in a two-stage synthesis proceeding from furan-2,5-dicarboxylic acid via the dichloride. A 250 ml three-neck flask with reflux condenser and dropping funnel was initially charged under argon with 72.1 g (462 mmol) of furan-2,5-dicarboxylic acid. Within a period of 10 min, 165 g (1.39 mol) of thionyl chloride with a few drops of added N,N-dimethylformamide were added. The suspension was heated to reflux temperature and the gas which formed was led off through wash bottles containing aqueous KOH solution. The mixture was then heated under reflux for 4 h until the evolution of gas had ended and the solid had dissolved completely. The product was isolated, after drawing off excess thionyl chloride, by distillative purification (T=110° C., p=0.0012 MPa). This resulted in 79.4 g of dichloride as a colourless crystalline solid (yield 89%) with a melting point of 79.5-80.0° C. Furan-2,5-dicarbonyl dichloride was stored under protective gas (argon) in the dark at room temperature until further use.

Preparation of the furan-2,5-dicarboxylic esters from furan-2,5-dicarbonyl dichloride (II)

Under argon, a three-neck flask with reflux condenser and dropping funnel was initially charged with the dichloride which was melted by heating. 2.4 equivalents of isoheptanol (isomer mixture; Exxal 7; Exxon Mobil) were slowly added dropwise to the liquid, which resulted in an exothermic reaction with evolution of gas. The gas formed was passed through wash bottles containing aqueous KOH solution. After complete addition, the mixture was stirred at a temperature of 80-100° C. for 16 h.

The excess alcohol was removed under reduced pressure in the presence of boiling granules, and the crude product was purified by distillation. This gave diheptyl furan-2,5-dicarboxylate, which was used for the further experiments.

Characterization of the diheptyl furan-2,5-dicarboxylate 1.1 Determination of Ester Purity by Means of Gas Chromatography Analysis (GC)

The determination of the purity of the esters prepared by means of GC is effected with a "6890N" GC machine from Agilent Technologies using a DB-5 column (length: 20 m, internal diameter: 0.25 mm, film thickness 0.25 μm) from J&W Scientific and a flame ionization detector under the following boundary conditions:

| | |
|---|---|
| Oven start temperature: 150° C. | Oven end temperature: 350° C. |
| (1) Heating rate 150-300° C.: 10 K/min | (2) Isothermal: 10 min. at 300° C. |
| (3) Heating rate 300-350° C.: 25 K/min. | |
| Total run time: 27 min. | |

| | |
|---|---|
| Injection block entrance temperature: 300° C. | Split ratio: 200:1 |
| Split flow rate: 512.2 ml/min | Total flow rate: 517.7 ml/min. |
| Carrier gas: helium | Injection volume: 3 microlitres |

| | |
|---|---|
| Detector temperature: 350° C. | Combustion gas: hydrogen |
| Hydrogen flow rate: 40 ml/min. | Air flow rate: 440 ml/min. |
| Makeup gas: helium | Makeup gas flow rate: 45 ml/min. |

The gas chromatograms obtained are evaluated manually against comparative substances present; the purity is reported in area percent. Due to the high final contents of target substance of >98%, the expected error resulting from lack of calibration for the particular test substance is low.

The measurement gave a purity of the ester prepared in Example 1 of 99.3 area %.

1.2 Determination of the Density of the Ester Prepared

The density of the esters prepared was determined by means of an oscillating U-tube to DIN 51757—method 4.

The measurement gave a density of 1.0075 g/cm$^3$.

1.3 Determination of the APHA Colour Number of the Ester Prepared

The colour number of the esters prepared was determined to DIN EN ISO 6271-2.

The measurement gave an APHA colour number of 8.

1.4 Determination of the Acid Number of the Ester Prepared

The acid number of the esters prepared was determined to DIN EN ISO 2114.

The determination gave an acid number of 0.012 mg KOH/g.

1.5 Determination of the Water Content of the Ester Prepared

The water content of the esters prepared was determined to DIN 51777 Part 1 (direct method)

The determination gave a water content of 0.023%.

1.6 Determination of the Intrinsic Viscosity of the Ester Prepared

The intrinsic viscosity (shear viscosity) of the ester prepared was determined using a Physica MCR 101 (from Anton-Paar) with a Z3 measurement system (DIN 25 mm) in rotation mode, by means of the following method:

Ester and measurement system were first equilibrated to a temperature 20° C., then the following actions were executed:

1. Preliminary shear at 100 s$^{-1}$ for a period of 60 s, in the course of which no measurements were recorded (to level out any thixotropic effects which occur and for better temperature distribution).

2. An upward frequency ramp commencing at 500 s$^{-1}$ and ending at 10 s$^{-1}$, divided into a logarithmic series of 20 steps each with measurement point duration 5 s (verification of newtonian behaviour).

The ester exhibited newtonian flow behaviour.

The measurement gave a shear viscosity (at 42 s$^{-1}$) of 90 mPa*s.

1.7 Determination of Glass Transition Temperature and Melting Point of the Ester Prepared by Means of DSC The glass transition temperature and the melting point were determined by means of differential calorimetry (DSC) to DIN 51007 (temperature range from −150° C. to +200° C.) from the first heating curve at a heating rate of 10 K/min. The turning point of the heat flow curve is evaluated as the glass transition temperature.

The measurement gave a glass transition temperature of −45° C. and a melting point of −19° C., the sample had been stored in liquid form at room temperature for 7 days beforehand.

Example 2

Dissolution Temperature of the Plasticizers

The dissolution temperature states the temperature from which a PVC powder dispersed in a continuously heated plasticizer excess (96 g of plasticizer to 4 g of polymer) is dissolved, and permits conclusions about the gelling characteristics. Di-(2-ethylhexyl)furan-2,5-dicarboxylate (D2EHFDC), di-n-hexyl furan-2,5-dicarboxylate (DN-HFDC) and di-n-butyl furan-2,5-dicarboxylate (DNBFDC) were prepared using 2-ethylhexanol and n-hexanol respectively, analogously to Example 1. Di-n-butyl furan-2,5-dicarboxylate and di-n-hexyl furan-2,5-dicarboxylate (DNHFDC) were first melted at 50° C., di-(2-ethylhexyl)furan-2,5-dicarboxylate (D2EHFDC) and the inventive diisoheptyl furan-2,5-dicarboxylate (DIHFDC) was heated to 50° C., before the PVC powder was dispersed in liquid and the temperature was increased.

Test Procedure:

96 g of the appropriate plasticizer and 4 g of the PVC Lacovyl PB 1704 H (from Arkema) are weighed into a 150 ml beaker. A magnetic stirrer bar and an internal thermometer secured to a clamp stand (range: 0° C.-250° C., display accuracy: 0.5° C.) are added to the mixture. A wire or adhesive tape is used to secure a paper strip bearing the message "Lösetemperatur" in the font "Times New Roman", font size 12, to the reverse side of the beaker such that the message can be seen through the beaker. Thereafter, the hotplate of a heatable laboratory stirrer unit (MR-Hei-Standard) is set to 200° C. and the speed to 600 rpm. On attainment of an internal temperature of the liquid of 140° C., the target temperature was once again raised to 250° C. The dissolution temperature has been attained when the message is just clearly readable through the liquid.

For the three abovementioned plasticizers, the following values shown in Table 1 were determined (double determination):

TABLE 1

Results of the tests of dissolution temperature

| Plasticizer | Dissolution temperature [° C.] |
|---|---|
| DNBFDC | 117 |
| DNHFDC | 104 |
| DIHFDC* | 112 |
| D2EHFDC | 120 |

*inventive

The sequence of the dissolution temperatures logically increases with rising ester chain length Compared to the DNHFDC present in solid form, the inventive DIHFDC, however, has much better processability and only a moderate increase in the dissolution temperature compared to DNHFDC is observed.

Example 3

Use of the Inventive Diheptyl Furandicarboxylates Alone and in a Blend with a further Plasticizer in a PVC Plastisol for Production of Topcoat Films for Floor Coverings: Production of the Plastisols The advantageous properties achievable with the inventive plasticizers are to be illustrated hereinafter using plastisols/pastes as used, for example, for production of a transparent top layer (called "topcoat") in floor coverings of multilayer structure. The starting weights used, in grams, of the components for the different pastes can be found in Table 2 below. Examples 4 and 6 are inventive; the other Examples 1, 2, 3, 5, 7 and 8 are comparative examples.

TABLE 2

| Formulation | 1 | 2 | 3 | 4* | 5 | 6* | 7 |
|---|---|---|---|---|---|---|---|
| Vestolit B 7021 -- Ultra | 100 | 100 | 100 | 100 | 100 | 100 | 100 |
| Vestinol ® 9 | 50 | | | | | | |
| Hexamoll ® DINCH | | 50 | 10 | 10 | 10 | | |
| DNHFDC | | | 40 | | | | |
| DIHFDC | | | | 40 | | 50 | |
| D2EHFDC | | | | | 40 | | 50 |
| Drapex 39 | 3 | 3 | 3 | 3 | 3 | 3 | 3 |
| Mark CZ 149 | 2 | 2 | 2 | 2 | 2 | 2 | 2 |

*= inventive

The substances used are described hereinafter:
Vestolit B 7021 - Ultra microsuspension PVC (homopolymer) with a K value (determined to DIN EN ISO 1628-2) of 70; from Vestolit GmbH.
Vestinol ® 9 diisononyl (ortho)phthalate (DINP), plasticizer; from Evonik Oxeno GmbH.
Hexamoll ® DINCH: diisononyl cyclohexanecarboxylate; BASF SE
DNHFDC: di-n-hexyl furan-2,5-dicarboxylate (prepared with n-hexanol analogously to Example 1)
DIHFDC: inventive diisoheptyl furandicarboxylate; according to Example 1
D2EHFDC: di-2-ethylhexyl furan-2,5-dicarboxylate (prepared with 2-ethylhexanol analogously to Example 1)
Drapex 39 epoxidized soybean oil; costabilizer with plasticizing action; from Galata Chemicals
Mark CZ 149: Ca/Zn stabilizer, from Galata Chemicals The liquid constituents were weighed into a PE beaker before the solid constituents. The mixture was stirred with an ointment spatula such that no unwetted powder was present any longer. The mixing beaker was then clamped into the clamping device of a dissolver stirrer. A mixer disc was used to homogenize the sample. This was done by increasing the speed from 330 rpm to 2000 rpm and stirring until the temperature on the digital display of the temperature sensor reached 30.0° C. This reliably ensured that the homogenization of the paste had been achieved with a defined energy input. Thereafter, the paste was equilibrated immediately at 25.0° C.

Formulation 3 was producible only by heating the furandicarboxylate present in solid form. After the preparation, however, the paste solidified to such a degree that no further processing was possible. A further comparative test with pure DNHFDC was then not carried out.

Paste 4 exhibits the mode of action of the inventive diheptyl furandicarboxylate in blends with the plasticizer Hexamoll® DINCH. Paste 6 exhibits the mode of action of the inventive diheptyl furandicarboxylate when used as the sole plasticizer.

Example 4

Use of the Inventive Diheptyl Furandicarboxylates in a PVC Plastisol for Production of Topcoat Films for Floor Coverings: Measurement of Paste Viscosity The measurement of the viscosities of the pastes produced in Example 3 was conducted with a Physica MCR 101 rheometer (from Anton Paar), which was controlled via the associated Rheoplus software, as follows.

The paste which had been stored after production at 25° C. for 24 h was homogenized once again with a spatula in the storage container and analyzed in the Z3 measurement system (diameter 25 mm) according to the operating instructions. The measurement was conducted isothermally at 25° C. The following actions were executed:

Preliminary shear of $100\ s^{-1}$ for a period of 60 s, in which no measurements were recorded (levelling out of thixotropic effects).

An isothermal downward ramp, commencing at a shear rate of $200\ s^{-1}$ down to $0.1\ s^{-1}$, divided into a logarithmic series with 30 steps each of measurement point duration 5 s. The results of the measurement are shown in Table 3.

TABLE 3

Results of the viscosity measurement (shear rate profile)

| | Plastisol formulation according to Ex. 3 | | | | | | |
|---|---|---|---|---|---|---|---|
| | 1 | 2 | 3 | 4* | 5 | 6* | 7 |
| Shear viscosity at shear rate = 100/s [Pa * s] | 6 | 3.5 | 17.3 | 7.7 | 7.8 | 9.5 | 9.7 |
| Shear viscosity at shear rate = 10/s [Pa * s] | 3 | 1.7 | 8 | 4.1 | 4.2 | 5.1 | 5.2 |
| Shear viscosity at shear rate = 1/s [Pa * s] | 3 | 1.6 | 7.5 | 4.1 | 3.9 | 4.9 | 4.8 |
| Shear viscosity at shear rate = 0.1/s [Pa * s] | 4.2 | 2 | 10.3 | 5.6 | 5.7 | 5.8 | 6.5 |
| Range of variation [%] (Max. visco – min. visco/min. visco) * 100 | 100 | 119 | 131 | 88 | 100 | 98 | 102 |

*= inventive

Compared to the pastes comprising only one plasticizer substance (pastes 1, 2, 6, 7), the inventive paste 6 has the smallest range of variation of the paste viscosity. With pure DNHFDC (solid) no PVC paste can be produced, and even the DNHFDC mixture with DINCH exhibits a very high paste viscosity, the determination of which is scarcely feasible at high shear rates with the measurement system used. A blend of the plasticizer Hexamoll® DINCH with the inventive diheptyl furandicarboxylate (paste 4) leads not only to a distinct reduction in the viscosity level of the paste but also to a very significant reduction in the range of variation compared to a paste comprising Hexamoll® DINCH alone as a plasticizer (paste 2). The general increase in the viscosity level of the inventive pastes can be matched easily by the person skilled in the art to the circumstances present in the particular processing method, for example by adding viscosity additives or solvents.

Plasticizers having outstanding gelation properties, especially what are called fast gelators, frequently exhibit inadequate viscosity stability in the PVC pastes produced therewith. The storage stability of PVC pastes is of great significance in that the pastes on the industrial scale are generally produced at a central site and then distributed gradually to the production plants (e.g. coating plants). Between production of the paste and processing thereof, periods of up to 7 days may pass.

In order to determine the storage stability of the pastes, viscosity measurements at a shear rate of 100 s$^{-1}$ were conducted after storage time 2 h, after storage time 24 h and after storage time 7 days. Between the measurements, the pastes were stored in a closed vessel at 25"C. The measurements were conducted as described above. The results are compiled in Table 4.

TABLE 4

Results of viscosity measurement (storage stability)

| | Plastisol formulation according to Ex. 3 | | | | | | |
|---|---|---|---|---|---|---|---|
| | 1 | 2 | 3 | 4* | 5 | 6* | 7 |
| Shear viscosity at shear rate = 100/s 2 hours after production of the plastisols [Pa * s] | 6 | 4.1 | 4.9 | 6.9 | 7.2 | 8.5 | 9 |
| Shear viscosity at shear rate = 100/s 24 hours after production of the plastisols [Pa * s] | 6 | 3.5 | 17.3 | 7.7 | 7.8 | 9.5 | 9.7 |
| Shear viscosity at shear rate = 100/s 7 days after production of the plastisols [Pa * s] | 6.4 | 3.5 | 18.6 | 8.4 | 8.3 | 10.9 | 10.8 |
| Range of variations [%] (7 d visco − 2 h visco/2 h visco) * 100 | +7 | −15 | +280 | +22 | +15 | +28 | +20 |

*= inventive

The results show that the storage stability requirement on the inventive diheptyl furandicarboxylates is met both as an individual substance (sample 6) and in the mixture with DINCH (sample 4). In contrast, the DNHFDC/DINCH mixture (sample 3) solidifies so severely with increasing storage that it is no longer processable.

Example 5

Use of the Inventive Diheptyl Furandicarboxylates in a PVC Plastisol for Production of Topcoat Films for Floor Coverings: Determination of Gelation Characteristics (Gelation Rate)

The study of the gelation characteristics of the pastes was conducted in the Physica MCR 101 in oscillation mode with a plate-plate measurement system (PP25), which was operated under shear stress control. An additional temperature control hood was attached to the system in order to achieve homogeneous heat distribution and a uniform sample temperature.

The following parameters were established:
Mode: Temperature gradient
    Start temperature: 25° C.
    End temperature: 180° C.
    Heating/cooling rate: 5° C./min
    Oscillation frequency: 4-0.1 Hz ramp logarithmic
    Angular frequency omega: 10 1/s
    Number of measurement points: 63
    Measurement point duration: 0.5 min
    Automatic gap readjustment F: 0 N
    Constant measurement point duration
    Gap width 0.5 mm
Measurement Procedure:

A drop of the paste to be analyzed, free of air bubbles, was applied with a spatula to the lower measurement system plate. It was ensured that, after the closure of the measurement system, some paste could exude uniformly out of the measurement system (not more than approx. 6 mm overall). Subsequently, the temperature control hood was positioned over the sample and the measurement was started. The "complex viscosity" of the paste was determined as a function of temperature. Since a particular temperature is attained within a period of time (fixed by the heating rate of 5° C./min), not only the gelation temperature but also a statement about the gelation rate of the system analyzed is obtained. Onset of the gelation process was noticeable by a sudden sharp rise in the complex viscosity. The sooner the onset of this viscosity rise, the better the gelation capacity of the system. By interpolating for each plastisol, the measurement curves obtained were used to determine the temperatures at which a complex viscosity of 1000 Pa*s or 10 000 Pa*s had been attained. In addition, by means of the tangent method, the maximum plastisol viscosity attained in the present test setup was determined, and, by dropping a perpendicular, the temperature from which the maximum plastisol viscosity occurs. The results are compiled in Table 5.

TABLE 5

Results of the gelation tests

| | Plastisol formulation (according to Ex. 3) | | | | | | |
|---|---|---|---|---|---|---|---|
| | 1 | 2 | 3 | 4* | 5 | 6* | 7 |
| Attainment of a plastisol viscosity of 1000 Pa * s at [° C.] | 87 | 114 | 71 | 78 | 81 | 76 | 79 |
| Attainment of a plastisol viscosity of 10 000 Pa * s at [° C.] | 96 | 134 | 74 | 82 | 86 | 79 | 83 |
| Maximum plastisol viscosity [Pa * s] | 27 900 | 19 500 | 67 800 | 48 000 | 31 400 | 62 000 | 46 800 |
| Temperature on attainment of the maximum plastisol viscosity [° C.] | 136 | 147 | 86 | 91 | 96 | 88 | 92 |

*= inventive

Compared to the pastes comprising only one plasticizer substance (pastes 1, 2, 6, 7), the inventive paste has the fastest gelation. The gelation also proceeds much more rapidly or at lower temperatures than the gelation of the VESTINOL® 9 paste. The maximum viscosities attainable during the gelling process are clearly the highest for the inventive sample. The same applies to the temperature at which the maximum paste viscosity is attained during the gelling process. This temperature is at its lowest for the inventive sample, and the margin from the to samples comprising Vestinol® 9 and DINCH is particularly large. Thus, the inventive diheptyl furandicarboxylates provide plasticizers which possess excellent gelation properties and whose PVC pastes can be gelated to give mouldings with high strength. The PVC compositions comprising the inventive plasticizers can especially be processed at high speeds and at low processing temperatures. The addition of a relatively low proportion of Hexamoll® DINCH, which leads to a significant reduction in the paste viscosity (see Ex. 4), exhibits only a minor influence on the gelation properties. With DINCH too, much faster gelation is still enabled than is the case with the standard plasticizer VESTINOL® 9.

Example 6

Use of the Inventive Diheptyl Furandicarboxylates in a PVC Plastisol for Production of Topcoat Films for Floor Coverings: Determination of the Shore a Hardness of Castings (Plasticizer Efficiency)

The Shore hardness is a measure of the softness of a test specimen. The further a standardized needle can penetrate into the test specimen with a particular measurement duration, the lower the measurement is. The plasticizer with the highest efficiency gives the lowest Shore hardness value for the same amount of plasticizer. Since formulations/recipes in practice are frequently adjusted or optimized toward a particular Shore hardness, it is accordingly possible in the case of very efficient plasticizers to dispense with a particular proportion in the formulation, which means a reduction in costs for the processor.

To determine Shore hardnesses, the pastes produced according to Example 3 were poured into round brass casting moulds with a diameter of 42 mm (starting weight: 20.0 g). Then the pastes were gelated in the moulds in a forced-air drying cabinet at 200° C. for 30 min, removed after cooling and, before the measurement, stored in a drying cabinet (25° C.) for at least 24 hours. The thickness of the discs was approx. 12 mm.

The hardness measurements were conducted to DIN 53 505 with a Shore A instrument from Zwick-Roell, the measurement being read off after 3 seconds in each case. Measurements were conducted at three different points on each test specimen (e.g. casting), and an average was formed. The results of the hardness determination are compiled in Table 6.

TABLE 6

Results of the Shore A measurements

| | Plastisol formulation (according to Ex. 3) | | | | | | |
|---|---|---|---|---|---|---|---|
| | 1 | 2 | 3 | 4* | 5 | 6* | 7 |
| Shore A | 82 | 84 | 75 | 78 | 80 | 77 | 79 |

*= inventive

Compared to the pastes comprising only one plasticizer substance (pastes 1, 2, 6, 7), the casting which was produced from the inventive paste 6 has the lowest Shore A hardness and thus the greatest "softness". Thus, esters having exceptionally high plasticizer efficiency in PVC mixtures are provided, which leads to a clear potential for savings with respect to the amount of plasticizer required compared to, for example, the standard plasticizer Vestinol® 9. Surprisingly, blending with the much less efficient DINCH (sample 4) only slightly lowers the plasticizer efficiency of the inventive esters, which is still far better than for the standard plasticizer.

Example 7

Use of the Inventive Diheptyl Furandicarboxylates in a PVC Plastisol for Production of Topcoat Films for Floor Coverings: Determination of Transparency and Yellowness Index of the Transparent Topcoat Films The films were produced after a maturing time of the plastisols of 24 hours (at 25° C.). For the film production, a roll nip of 1.40 mm was established on the doctor roll of a Mathis Labcoater (manufacturer: W. Mathis AG). This nip was monitored by a feeler gauge and readjusted as necessary. The pastes produced were doctored onto a high-gloss paper (Ultracast Patent; from Sappi Ltd.) clamped flat in a frame by means of the doctor roll of the Mathis Labcoater. The plastisol applied by doctoring was then gelated fully at 200° C. in the Mathis oven for 2 min. After cooling, the film thickness was determined with an accuracy of 0.01 mm with the aid of a rapid thickness gauge (KXL047; from Mitutoyo). The film thickness of this film at the roll nip specified was in all cases between 0.95 and 1.05 mm. The measurement of the thickness was conducted at three different points on the film.

Transparency is an important criterion for assessing the quality of PVC topcoats in the flooring sector, since an optimal overall appearance can be achieved only with high transparency (=low opacity). The transparency of a PVC topcoat film is also considered to be a measure of the compatibility of the formulation constituents used for film production, more particularly to be a measure for assessing the compatibility of PVC matrix and plasticizer. High transparency (=low opacity) generally means good compatibility. The opacity was determined with a "Spectra Guide" instrument from Byk Gardner. As a background for the opacity measurements, a white tile and a black tile were used. The opacity measurement was selected via the menu on the colorimeter. The measurements themselves were conducted at 3 different points on the samples and evaluated automatically (average value).

The yellowness index is a further important quality criterion. Yellowing in the topcoat can lead to considerable visual impairment of a floor finish, and therefore only very low yellowness indices can generally be tolerated in a PVC topcoat. The yellowing can be caused firstly by formulation constituents (and also by the by-products and degradation products thereof), and secondly by degradation (for example thermooxidative) during the production process and/or during the use of the topcoat or of the floor covering.

The yellowness index (index YD 1925) is a measure of the yellowing of a test specimen. The colour was analyzed with a "Spectro Guide" instrument from Byk-Gardner. As a background for the colour measurements, a white reference tile was used. The following parameters were set:
Illuminant: C/2°
Number of measurements: 3
Display: CIE L*a*b*
Index measured: YD1925

The measurements themselves were conducted at 3 different points on the samples (for effect and smooth foams in the case of a plastisol doctoring thickness of 200 μm). The values from the 3 measurements were averaged. Table 7 shows the results.

TABLE 7

Opacity and yellowness index of transparent topcoat films

| | Plastisol formulation (according to Ex. 3) | | | | | | |
|---|---|---|---|---|---|---|---|
| | 1 | 2 | 3 | 4* | 5 | 6* | 7 |
| Opacity [—] | 10.2 | 9.9 | n.da. | 9.9 | 9.8 | 10.1 | 9.9 |
| Yellowness index [—] | 9.0 | 9.0 | n.da. | 8.5 | 9.6 | 9.0 | 10.3 |

*= inventive;
n.da. = not determinable, sample highly inhomogeneous.

The inventive diheptyl furandicarboxylates (Examples 4 and 6), both in the form of an individual substance and in the form of a mixture with DINCH, exhibit excellent compatibility with PVC, expressed by very low opacity values. In addition, very low yellowness indices are likewise achieved both in the form of an individual substance and in the form of a mixture with DINCH. This is surprising in that plasticizers produced on the basis of renewable raw materials, especially of sugars, generally have high yellowness indices. The comparative sample comprising DNHFDC (sample 3), in contrast, is inhomogeneous and unsuitable for the application intended in the present case (transparent floor topcoat).

Example 8

Use of the Inventive Diheptyl Furandicarboxylates in a PVC Plastisol for Production of Topcoat Films for Floor Coverings: Water Storage (at 30° C.) and Hot Storage (at 80° C.) of the Topcoat Films Ageing stability under different ambient conditions is a further essential quality criterion for PVC plasticizers. Especially behaviour towards water (water absorption & washout characteristics of formulation constituents) and with respect to elevated temperatures (vaporization of formulation constituents & thermal ageing) gave an insight into ageing stability.

If plastic flooring absorbs water to any great extent, this firstly alters the material properties thereof, and secondly also the visual appearance thereof (for example opacification). A high water absorption is accordingly generally undesirable. Washout characteristics are an additional criterion for the permanence of the formulation constituents under use conditions. This is especially true of stabilizers, plasticizers and/or constituents thereof, since a reduction in concentration in the plastic flooring in the case of these formulation constituents can both worsen the material properties and severely reduce the lifetime of the floor covering.

For the determination of water stability, gelated 1 mm polymer films (gelation conditions in the Mathis oven: 200° C./2 min) were used. The test specimens were circles of diameter 3 cm cut out of the films. Before the water storage, the test specimens were stored in a desiccator equipped with desiccant (KC-Trockenperlen, from BASF SE) at 25° C. for 24 hours. The starting weight was determined accurately to 0.1 mg with an analytical balance. The test specimens were then stored below the water surface with sample holders in an agitated bath filled with demineralized water ("WNB 22" model with "CDP" Peltier cooling apparatus; from Memmert GmbH) at a temperature of 30° C. for 7 days, and moved continuously. After the storage, the circles were removed from the water bath, dried and weighed (=weight after 7 days). The difference from the starting weight was used to calculate the water absorption. After the final weighing, the test specimens were again stored at 25° C. in a desiccator equipped with desiccant (KC-Trockenperlen) for 24 hours and then weighed once again (final weight=weight after drying). The difference from the starting weight was used to calculate the loss of mass by water storage (=loss as a result of washing out).

For the determination of the stability to thermal ageing, test specimens were produced as described above. The test specimens were predried and weighed as described above, and the yellowness index was also determined as described in Ex. 7. Subsequently, the test specimens were stored in a drying cabinet at 80° C. for one week. Thereafter, the loss of mass of the test specimens and, again, the yellowness index thereof were determined. The results are compiled in Table 8.

TABLE 8

Results of the studies of ageing stability

| | Plastisol formulation (according to Ex. 3) | | | | | | |
|---|---|---|---|---|---|---|---|
| | 1 | 2 | 3 | 4* | 5 | 6* | 7 |
| Water absorption after 7 days at 30° C. [ma %] | 1.1 | 1.2 | 1.2 | 1.2 | 1.1 | 1.2 | 1.1 |
| Washout loss after 7 days at 30° C. [ma %] | 0 | 0 | 0.1 | 0 | 0 | 0 | 0 |
| Loss of mass after 7 days at 80° C. [ma %] | 0 | 0.1 | 3.4 | 1.5 | 0.6 | 1.6 | 0.7 |
| Yellowness index before heat storage | 9.0 | 9.0 | n.da. | 8.5 | 9.6 | 9.0 | 10.3 |
| Yellowness index after 7 days at 80° C. | 20.7 | 23.3 | n.da. | 20.5 | 22.9 | 21 | 24.2 |

*= inventive;
n.da.: not determinable, sample highly inhomogeneous

The water absorption of all samples is at the same level as for the standard plasticizer Vestinol® 9. No washout is detectable in any case. The water stability of the inventive diheptyl furandicarboxylates can thus be assessed as excellent.

In the course of hot storage at 80° C., in contrast, great differences are found between the samples. Surprisingly, the inventive test specimen 4 exhibits a much lower loss of mass than the test specimen (3) comprising DNHFDC (ester groups having 6 carbon atoms). Test specimens comprising the inventive plasticizer thus have much better stability at elevated temperature. With regard to discoloration, compared to the samples comprising only one plasticizer substance (1, 2, 6, 7), the sample comprising the inventive diheptyl furandicarboxylates surprisingly exhibits only slight yellowing as a result of thermal stress and is thus at the same level as the sample comprising the standard plasticizer Vestinol® 9, and surprisingly much better than the DINCH sample. This is astonishing because plasticizers based entirely or partly on renewable raw materials (especially sugars) are generally much more prone to yellowing at relatively high temperatures.

Thus, esters which lead in gelated PVC films to exceptionally good stability with respect to water, and excellent thermal stability, are provided.

Example 9

Use of the Inventive Diheptyl Furandicarboxylates in a PVC Plastisol for Production of Topcoat Films for Floor Coverings: Determination of Flexibility (DMTA)

DMTA analyses to DIN 65583 were conducted on test specimens which were produced from gelated films (film production according to Ex. 7 in a Mathis oven at 200° C./2 min). For the dynamic-mechanical-thermal analysis (DMTA), by applying an oscillating force to a test specimen, the viscoelastic properties are detected in a frequency-dependent and temperature-dependent manner, and the elastic modulus and damping values are determined. The maximum loss of modulus is evaluated as the glass transition temperature. Table 9 below shows the results.

TABLE 9

Results of the DMTA analyses

| | Plastisol formulation (according to Ex. 3) | | | | | | |
|---|---|---|---|---|---|---|---|
| | 1 | 2 | 3 | 4* | 5 | 6* | 7 |
| Glass transition point [° C.] | −38 | −43 | −32 | −28 | −30 | −24 | −26 |
| Storage modulus at +30° C. [MPa] | 11 | 19 | 7 | 4 | 8 | 6 | 8 |
| Storage modulus at 0° C. [MPa] | 92 | 116 | 59 | 97 | 101 | 109 | 114 |
| Storage modulus at −30° C. [MPa] | 716 | 646 | 803 | 1036 | 1059 | 1221 | 1129 |

*= inventive

Compared to the test specimens comprising only one plasticizer substance (pastes 1, 2, 6, 7), the test specimen which has been produced from inventive paste 6 surprisingly has the highest flexibility (i.e. the lowest storage modulus) at +30° C. Considering the blends with DINCH (pastes 3, 4, 5), for the test specimen comprising the inventive diheptyl furandicarboxylates (sample 4) at +30° C., a higher flexibility (i.e. a lower storage modulus) is evident than both for the test specimen comprising linear DNHFDC (sample 3) and for the test specimen comprising the singly branched D2EHFDC (sample 5), even though they have a much higher degree of branching than D2EHFDC. In addition, the inventive sample also has a likewise much higher flexibility compared to the D2EHFDC sample at 0° C. and at −30° C. This is all the more astonishing in that the glass transition temperature of the inventive sample is higher compared to the two other samples, and the flexibility of flexible PVC test specimens generally rises with decreasing glass transition temperature.

The invention claimed is:

1. A composition, comprising at least two isomeric diheptyl furan-2,5-dicarboxylates, wherein each diheptyl furan-2,5-dicarboxylate independently satisfies at least one property selected from the group consisting of
   a density of the diheptyl furan-2,5-dicarboxylate at 20° C. is not more than 1.1 g/cm$^3$,
   an intrinsic viscosity of the diheptyl furan-2,5-dicarboxylate at 25° C. is not more than 120 mPa*s, and
   when analyzed with a differential calorimeter, the diheptyl furan-2,5-dicarboxylate has no melting signal at temperatures greater than 20° C.

2. The composition according to claim 1, wherein at least one of the isomeric diheptyl furan-2,5-dicarboxylates satisfies all of the properties.

3. The composition according to claim 1, wherein at least one of the isomeric diheptyl furan-2,5-dicarboxylates satisfies at least two of the properties.

4. A plasticizer or plasticizer composition, comprising the composition according to claim 1.

5. The plasticizer or plasticizer composition according to claim 4, wherein none of the at least two isomeric diheptyl furan-2,5-dicarboxylates are present in a proportion of more than 99.9% by weight in an ester mixture.

6. The plasticizer or plasticizer composition according to claim 4, wherein at least one isomeric diheptyl furan-2,5-dicarboxylate comprises a heptyl group selected from the group consisting of n-heptyl, 2-methylhexyl, 3-methylhexyl, 4-methylhexyl, 5-methylhexyl, 2,2-dimethylpentyl, 2,3-dimethylpentyl, 3,3-dimethylpentyl, 2,4-dimethyl pentyl, 3-ethylpentyl, 2,2,3-trimethylbutyl, and 2-ethyl-3-methylbutyl.

7. The plasticizer composition according to claim 4, further comprising at least one additional plasticizer selected from the group consisting of an alkyl benzoate, a dialkyl adipate, a glyceryl ester, a trialkyl citrate, an acylated trialkyl citrate, a trialkyl mellitate, a glycol dibenzoate, a dialkyl terephthalate, a dialkyl phthalate, a dialkanoyl ester of isosorbitol, and a dialkyl ester of 1,2-, 1,3- or 1,4-cyclohexanedicarboxylic acid.

8. A process of preparing the composition of claim 1, the process comprising:
contacting a furandicarboxylic acid or a derivative thereof with an aliphatic alcohol having 7 carbon atoms, thereby obtaining a reaction mixture; and
heating the reaction mixture to a temperature of greater than 50° C. and esterifying or transesterifying the reaction mixture while removing a low molecular weight substance from the reaction mixture.

9. A process of preparing the composition according to claim 1, the process comprising:
contacting a 5-hydroxymethylfurfural, a furan derivative thereof, or a combination thereof with an aliphatic alcohol having 7 carbon atoms, a catalyst, and an oxygen-containing component, thereby obtaining a reaction mixture; and
adjusting the reaction mixture to a temperature of greater than 0° C. and conducting an oxidative esterification.

10. A polymer composition, comprising the composition according to claim 1 and at least one polymer.

11. The polymer composition according to claim 10, wherein the at least one polymer is selected from the group consisting of polyvinyl chloride (PVC), polyvinylidene chloride (PVDC), a polyacrylate, a fluoropolymer, polyvinyl acetate (PVAc), polyvinyl alcohol (PVA), a polyvinyl acetal, a polystyrene polymer, acrylonitrile-styrene-acrylate (ASA), styrene acrylonitrile (SAN), acrylonitrile-butadiene-styrene (ABS), styrene-maleic anhydride copolymer (SMA), styrene-methacrylic acid copolymer, a polyolefin, polyethylene-vinyl acetate (EVA), a polycarbonate, polyethylene terephthalate (PET), polybutylene terephthalate (PBT), polyoxymethylene (POM), polyamide (PA), polyethylene glycol (PEG), polyurethane (PU), thermoplastic polyurethane (TPU), a polysulphide (PSu), a biopolymer, polyhydroxybutyral (PHB), polyhydroxyvaleric acid (PHV), a polyester, starch, cellulose, a cellulose derivative, rubber, silicone, a mixture or copolymer thereof or of monomeric units thereof.

12. The polymer composition according to claim 10, comprising a plasticizer in an amount of from 5 to 200 parts by mass per 100 parts by mass of the polymer composition.

13. The polymer composition according to claim 10, comprising a copolymer of vinyl chloride with at least one monomer selected from the group consisting of vinylidene chloride, vinyl acetate, vinyl propionate, vinyl butyrate, vinyl benzoate, methyl acrylate, ethyl acrylate, and butyl acrylate.

14. A molding or film comprising the polymer composition according to claim 10.

15. The molding or film according to claim 14, wherein the film or molding is a floor covering, a wall covering, a hose, a profile, a polymer film, a roofing sheet, a sealing sheet, a cable or wire sheath, a tarpaulin, an advertising banner, synthetic leather, packaging film, a medical article, a toy, a seal, or a furnishing article.

16. A process of plasticizing a polymer, the process comprising plasticizing a polymer with the plasticizer or plasticizer composition of claim 4.

17. The process of claim 16, wherein the polymer is suitable for an adhesive, sealing compound, coating material, lacquer, paint, plastisol, paste, synthetic leather, floor covering, underbody protection, fabric coating, wallpaper, or ink.

* * * * *